(12) United States Patent
Plaian et al.

(10) Patent No.: US 9,078,602 B2
(45) Date of Patent: Jul. 14, 2015

(54) FUNDUS CAMERA

(75) Inventors: Andrei Plaian, Ponte San Nicolò (IT); Paola Griggio, Padua (IT); Anna D'Errico, Nimis (IT); Carlo Pellizzari, Vigonza (IT)

(73) Assignee: Centervue S.P.A., Padua (IT)

( * ) Notice: Subject to any disclaimer, the term of this patent is extended or adjusted under 35 U.S.C. 154(b) by 242 days.

(21) Appl. No.: 13/580,887

(22) PCT Filed: Jan. 27, 2011

(86) PCT No.: PCT/EP2011/051135
§ 371 (c)(1),
(2), (4) Date: Sep. 11, 2012

(87) PCT Pub. No.: WO2011/104062
PCT Pub. Date: Sep. 1, 2011

(65) Prior Publication Data
US 2013/0010261 A1     Jan. 10, 2013

(30) Foreign Application Priority Data

Feb. 25, 2010    (IT) .............................. TV2010A0025

(51) Int. Cl.
*A61B 3/14* (2006.01)
*A61B 3/12* (2006.01)

(52) U.S. Cl.
CPC ........................................ *A61B 3/12* (2013.01)

(58) Field of Classification Search
USPC ................................. 351/206, 210, 221, 215
See application file for complete search history.

(56) References Cited

U.S. PATENT DOCUMENTS

| 4,533,222 | A | 8/1985 | Ishikawa |
| 5,268,922 | A | 12/1993 | Fouere et al. |

(Continued)

FOREIGN PATENT DOCUMENTS

| EP | 0392743 A1 | 10/1990 |
| EP | 1340451 A2 | 9/2003 |

(Continued)

*Primary Examiner* — Ricky Mack
*Assistant Examiner* — Mustak Choudhury
(74) *Attorney, Agent, or Firm* — Novak Druce Connolly Bove + Quigg LLP

(57) ABSTRACT

The present invention refers to a fundus camera comprising:
  illuminating means that project a first light beam to illuminate the retina of a patient's eye, said illuminating means comprising one or more first light sources operatively associated with a shaped structure provided with a through hole;
  projecting means that project one or more second light beams on the patient's retina, said projecting means comprising one or more second light sources;
  sensor means for receiving the light reflected by the retina in line with a receiving surface in order to acquire one or more images of the retina;
  regulating means for adjusting the focus of the images of the retina, in line with the receiving surface of said sensor means;
  actuating means designed to move said regulating means and projecting means;
  processing means for analyzing the images of the retina acquired by said sensor means, and for generating control signals for said actuating means.

The projecting means are arranged coaxially with said illuminating means, along a same axis (a), and project said second light beams through at least a lens that is kept in position by means of a hollow body, which is operatively associated to said through hole.

23 Claims, 11 Drawing Sheets

(56) References Cited

U.S. PATENT DOCUMENTS

| | | |
|---|---|---|
| 6,337,993 B1 | 1/2002 | Kishida et al. |
| 2004/0252276 A1 | 12/2004 | Nanjo et al. |
| 2007/0291229 A1 | 12/2007 | Yamaguchi et al. |
| 2008/0123050 A1* | 5/2008 | Tanaka et al. .......... 351/206 |
| 2008/0231808 A1 | 9/2008 | Van de Velde |
| 2009/0153797 A1* | 6/2009 | Allon et al. .......... 351/206 |

FOREIGN PATENT DOCUMENTS

| | | |
|---|---|---|
| EP | 1864609 A1 | 12/2007 |
| EP | 2106741 A1 | 10/2009 |
| GB | 2359375 A | 8/2001 |
| WO | WO-99/20173 A1 | 4/1999 |
| WO | WO-2006/052479 A2 | 5/2006 |
| WO | WO-2008/101359 A1 | 8/2008 |

* cited by examiner

FUNDUS CAMERA

CROSS REFERENCE TO RELATED APPLICATIONS

This application is a National Phase filing under 35 U.S.C. §371 of PCT/EP2011/051135 filed on Jan. 27, 2011; and this application claims priority to Application No. TV2010A000025 filed in Italy on Feb. 25, 2010 under 35 U.S.C. §119; the entire contents of all are hereby incorporated by reference.

The present invention relates to the field of equipment for inspecting the ocular fundus.

In particular, the present invention refers to an apparatus for inspecting the ocular fundus that affords an improved performance inasmuch as concerns the procedure for focusing on the patient's retina.

It is common knowledge that apparatuses, commonly known as fundus cameras, are used to inspect the ocular fundus.

Typically, a fundus camera optically conjugates the pupil of the eye with a ring-shaped light source.

The eye is illuminated by a light beam that has a ring-shaped cross section on a level with the pupil and the light reflected by the retina is received, through the central portion of the pupil, by suitable sensor means designed to enable the retina to be observed and photographed.

Before starting an examination, a fundus camera must typically complete a procedure for focusing on the retina, so as to enable an optimal view of the latter.

The term "focusing" is used hereinafter to mean a set of steps designed to optically conjugate the above-mentioned sensor means with the patient's retina, adjusting for any refractory defects of the eye being examined, e.g. myopia or hypermetropia.

Figure 1:
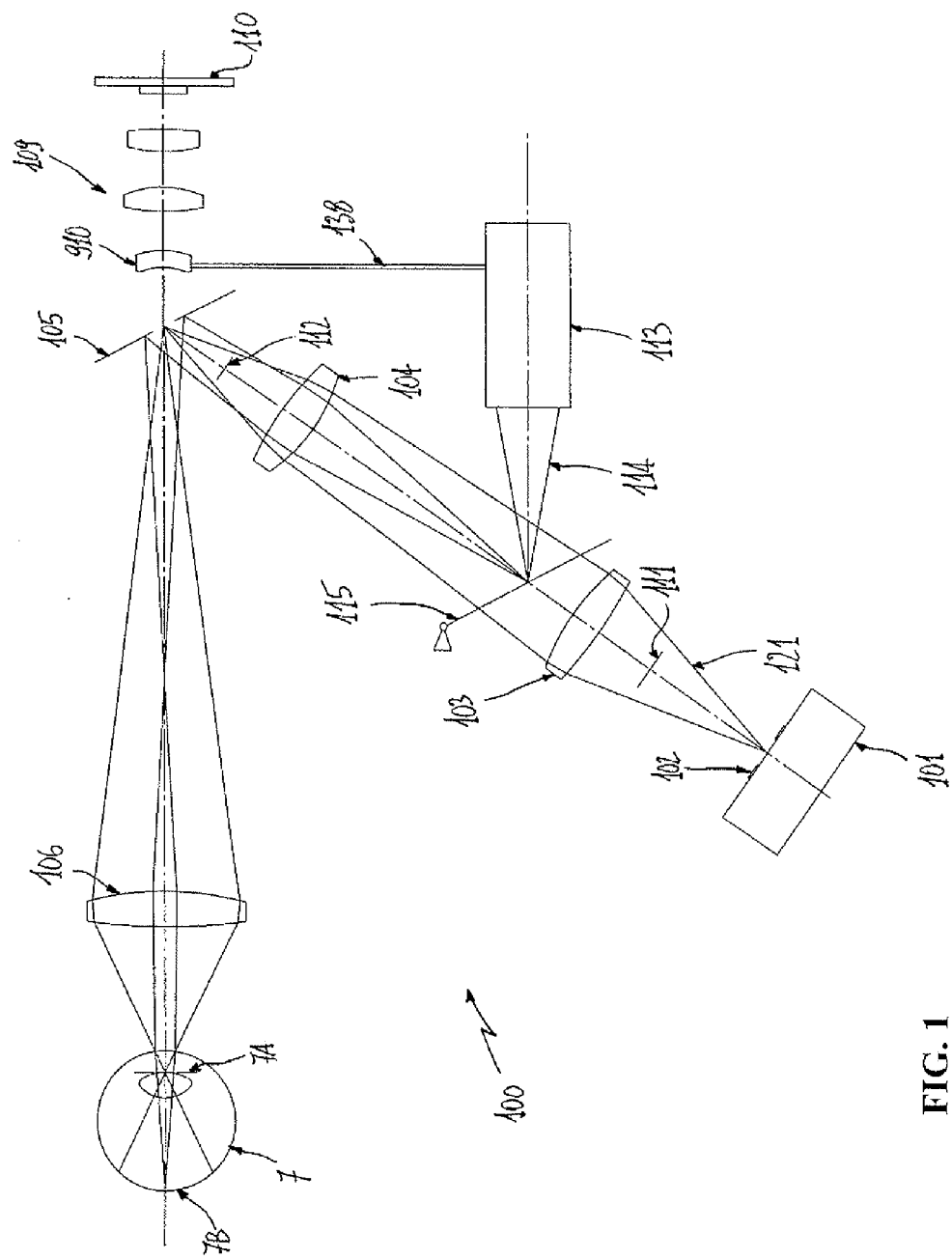

FIG. 1 is a schematic illustration of a fundus camera 100 of known type.

The camera 100 comprises an illuminator device 101 capable of emitting a ring-shaped light beam 121.

The light 121 emitted by the ring-shaped area 102 of the illuminator 101 is collimated in an area approximately coinciding with the centre of the perforated mirror 105 by means of a system of lenses 103 and 104.

The light beam 121 is reflected by the mirror 105 and collimated by means of the lens 106 on a point situated approximately on the plane of the pupil 7A of the eye 7, until it comes to illuminate the retina 7B.

The light reflected by the retina 7B passes through the central area of the pupil 7A and is oriented by the lens 106 towards the hole in the mirror 105, and then collimated by means of a set of lenses 109 to form an image on a receiving surface of the sensor 110, for example a digital camera.

Along the optical path of the light beam 121 there are also a first opaque disc 111, which intercepts the portions of light beam that might be reflected on the crystalline lens of the eye 7, and a second opaque disc 112, which intercepts the light that could give rise to reflections on the cornea of the eye 7.

The camera 100 comprises an emitter device 113, consisting of an infrared light source, one or more perforated masks, lenses and microprisms (not shown) for emitting a plurality of light beams 114 designed to generate a pattern of luminous lines on the retina.

The light beams 114 are inserted in the optical path of the camera 100 by means of a movable mirror 115 or, alternatively, a beam splitting device (not shown).

The emitter device 113 is operatively associated with the set of lenses 109, by means of a mechanical connection 138, such that any movement of the emitter 113 is mechanically synchronised with the movement of the whole set of lenses 109, or with the movement of one lens 910 in said set of lenses 109.

The luminous lines projected onto the retina by the light beam 114 are visible directly on the image returned by the sensor 110, or through an eyepiece operatively associated with a system of lenses and beam splitting devices (not shown).

Initially, a plurality of unaligned luminous lines is projected onto the retina.

In order to focus the fundus camera, the emitter device 113 and the set of lenses 109 are moved in a synchronous manner to align the luminous lines observable on the retina.

The fundus camera of conventional type, as illustrated in FIG. 1, has some drawbacks.

The use of a movable mirror 115 or beam splitter device to insert the luminous beams 114 in the optical path of the camera 100 is a complicated solution that proves costly to put into practice.

The movable mirror 115 may suffer from wear and tear after a relatively large number of usage cycles, with a negative fallout on the accuracy of its insertion in the optical path of the camera 100.

This can clearly interfere with the precision focusing of the camera 100.

On the other hand, using a beam splitter device permanently inserted in the optical path determines a dispersion of the light 121, projected by the illuminator device 101.

This makes it necessary to oversize the light emitting power of the illuminator device 101, with a corresponding increase in the cost of manufacturing the camera.

The adoption of a set of microprisms to separate the light emitted by the infrared light source into a plurality of beams 114, considerably complicates the production of the emitter device 113, with a further increase in the related costs.

The camera 100 is suitable for being focused manually by a human operator looking through an eyepiece.

In the event of autofocusing, however, any focusing procedure must necessarily involve steps for identifying the shape and position of the luminous lines projected onto the retina.

Such identification procedures are generally not very reliable, e.g. in cases where two luminous lines are near the position of alignment, or when the shape of the retina determines a change in the shape of the luminous lines.

The procedure for focusing the camera 100 is consequently difficult to implement with the aid of a software that enables it to be done automatically.

The main technical aim of the present invention is thus to provide a fundus camera that enables the above-mentioned drawbacks of the known art to be overcome.

Within the context of said technical aim, one object of the present invention is to provide a fundus camera that enables a simple and reliable focusing procedure to be completed easily and automatically by means of software.

Another object of the present invention is to provide a fundus camera characterised in that it is extremely simple to manufacture and of limited overall dimensions.

Another object of the present invention is to provide a fundus camera that is easy to manufacture industrially at competitive prices.

This technical aim and these objects, as well as others that will become evident from the description given below and the attached drawings, are achieved according to the invention by a fundus camera according to claim 1, as explained below.

The fundus camera according to the invention comprises illuminating means that project a first light beam to illuminate the retina of a patient's eye and that comprise one or more first light sources, preferably a plurality of LED (Light Emitting Diodes) devices.

The illuminating means comprise a shaped structure provided with a through hole.

The first light sources of the illuminating means are preferably arranged on said shaped structure, advantageously in a region around said through hole, so that the illuminating means emit a substantially ring-shaped light beam.

The fundus camera according to the invention comprises projecting means that project one or more second light beams onto the retina, said projecting means comprising one or more second light sources.

Preferably, the projecting means comprise an infrared light source, e.g. at least one infrared LED device, and an opaque mask with one or more holes for enabling the passage of the light emitted by said infrared light source.

The projecting means preferably also comprise a collimating lens positioned between the infrared light source and the opaque mask, and advantageously arranged so as to afford a relatively high spherical aberration.

The fundus camera according to the invention also comprises sensor means designed to receive the light reflected from the retina onto a receiving surface and thus acquire one or more images of the retina, and means for regulating the focusing of the images of the retina on a level with the receiving surface of said sensor means.

In the fundus camera according to the invention, there are also actuating means designed to move said regulating means and said projecting means, as well as processing means that analyse the images of the retina acquired by said sensor means and generate control signals for said actuating means.

According to the invention, the projecting means of the fundus camera are arranged coaxially to the illuminating means, along a same axis (a), and project said second light beams through at least a lens that is kept in position by means of a hollow body, which is operatively associated to the through hole of the shaped structure of the illuminating means of the fundus camera.

The projecting means can thus project the second light beams through the hole in the shaped structure of said illuminating means, which supports the first light sources of said illuminating means.

According to an aspect of the invention, the processing means calculate data indicative of the maximum light intensity values in one or more images of the retina and, on the strength of the data thus calculated, to generate control signals for said actuating means in order to move said regulating means into a focused position, coinciding with which the retina is optically conjugated with the receiving surface of said sensor means.

The data indicative of the maximum light intensity values preferably comprise a characteristic index of the points of maximum light intensity in one or more images of the retina.

According to a preferred embodiment of the present invention, said processing means complete a procedure that comprises at least the following steps:

i) analysing an image of the retina acquired by said sensor means;
ii) determining a number of points of maximum light intensity on said image of the retina, which is equal to the number of the second light beams projected by said projecting means;
iii) calculating a value of a characteristic index of said points of maximum light intensity;
iv) storing the value of said characteristic index calculated in the previous step (iii), and the corresponding position of said regulating means;
v) generating control signals for said actuating means in order to move said regulating means and said projecting means in a synchronised manner and with a pre-defined step;
vi) repeating the previous steps from (i) to (v) at least once;
vii) calculating the maximum value ($I_{MAX}$) of said characteristic index;
viii) generating control signals for said actuating means in order to move said regulating means into the position coinciding with which said characteristic index acquires said maximum value.

Preferably, said regulating means and said projecting means are moved by said actuating means in a synchronised manner, according to a function $Y=f(X)$, where X is the position of said regulating means and Y is the position of said projecting means.

According to one embodiment of the present invention, the regulating means and projecting means are operatively connected to one another by means of a kinematic chain and can advantageously be moved by a same first actuating device.

Alternatively, the above-mentioned actuating means may comprise a second actuating device for moving the regulating means, and a third actuating device for moving the projecting means.

In this case, the processing means advantageously control said actuating devices in order to move said regulating means and said projecting means in a synchronised manner, according to a function $Y=f(X)$ that can advantageously be defined by means of a suitable fundus camera calibration procedure.

Another aspect of the present invention relates to a method for focusing the fundus camera on the retina of the patient's eye, which comprises the following steps:

I) projecting said second light beams onto the retina by means of said projecting means;
II) acquiring an image of the retina;
III) determining a number of points of maximum light intensity on said image of the retina, which is equal to the number of the second light beams projected by said projecting means;
IV) calculating a value of a characteristic index of said points of maximum light intensity;
V) moving said regulating means and said projecting means in a synchronised manner and with a predefined step;
VI) repeating the previous steps (I) to (V) at least once;
VII) calculating the maximum value of said characteristic index; and
VIII) moving said regulating means into the position coinciding with which said characteristic index acquires said maximum value.

Figure 2:
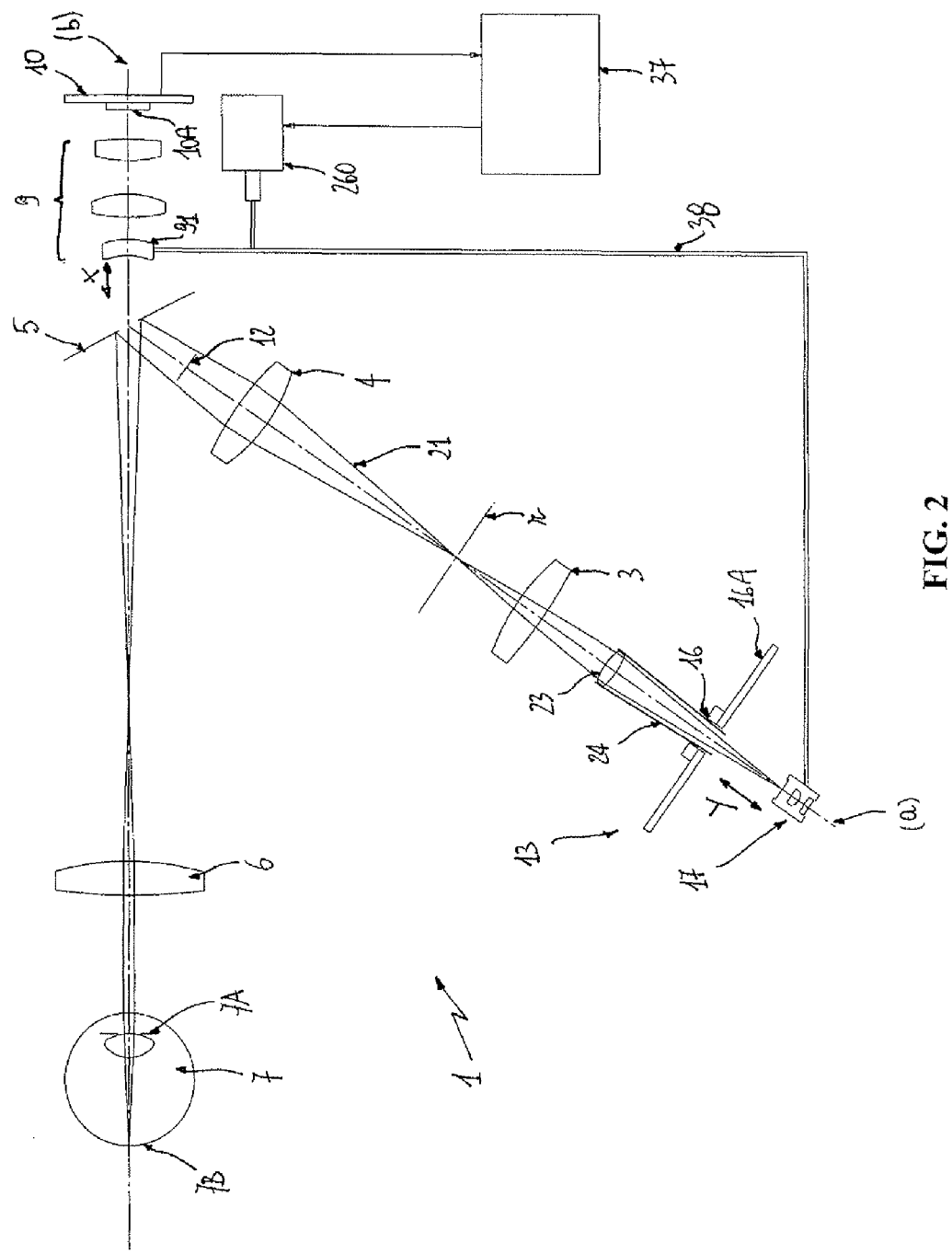
Figure 3:
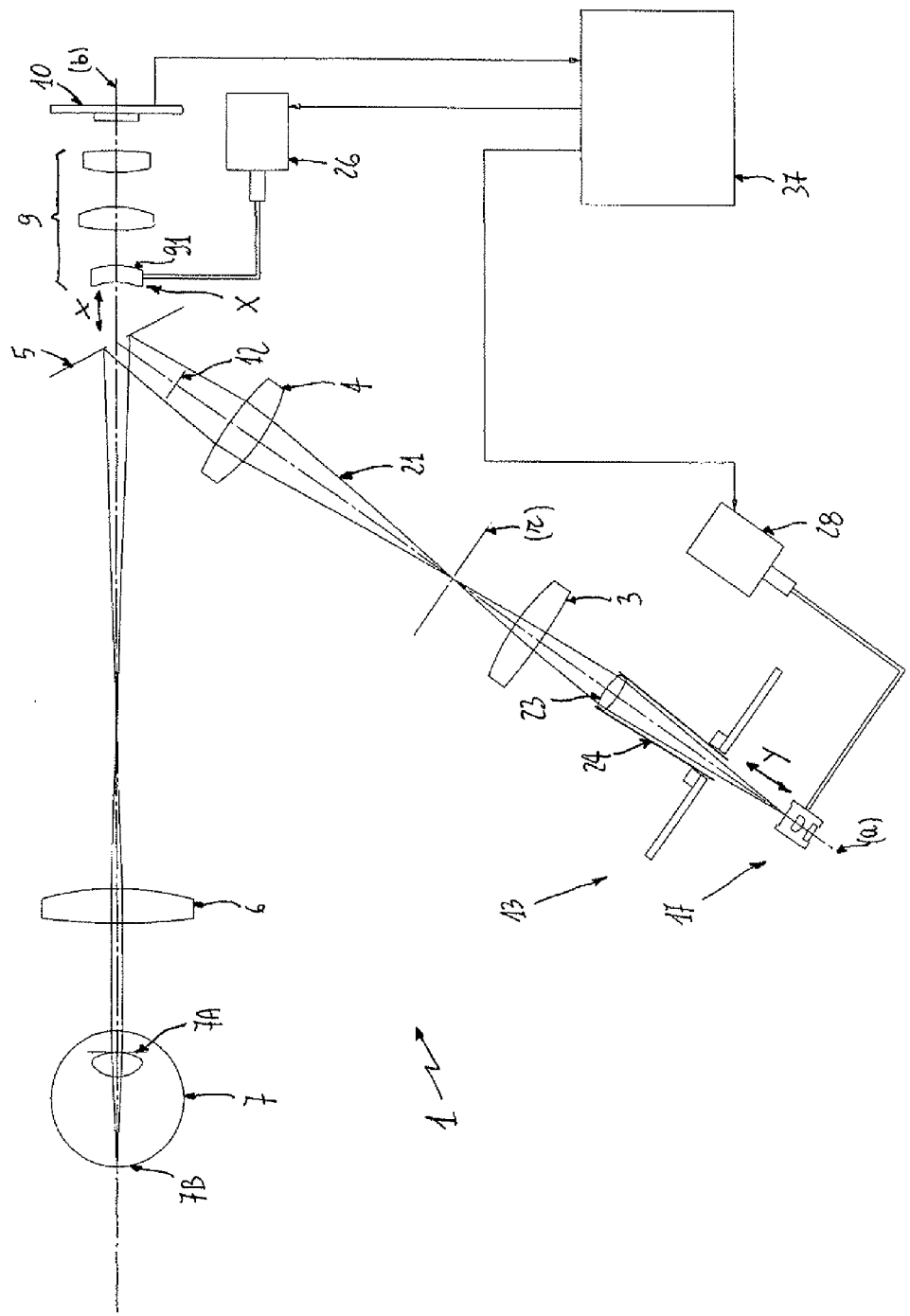
Figure 4:
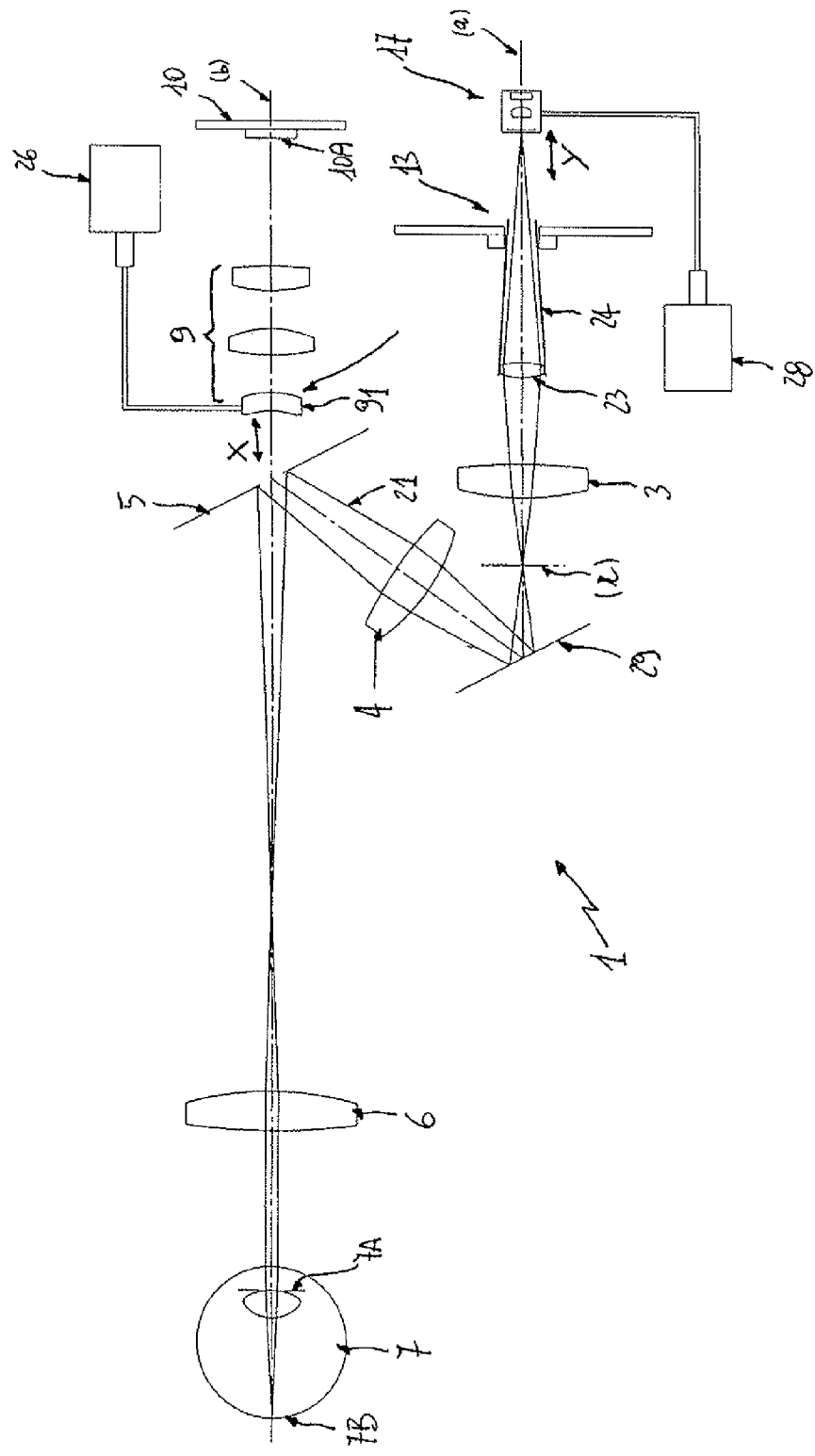
Figure 5:
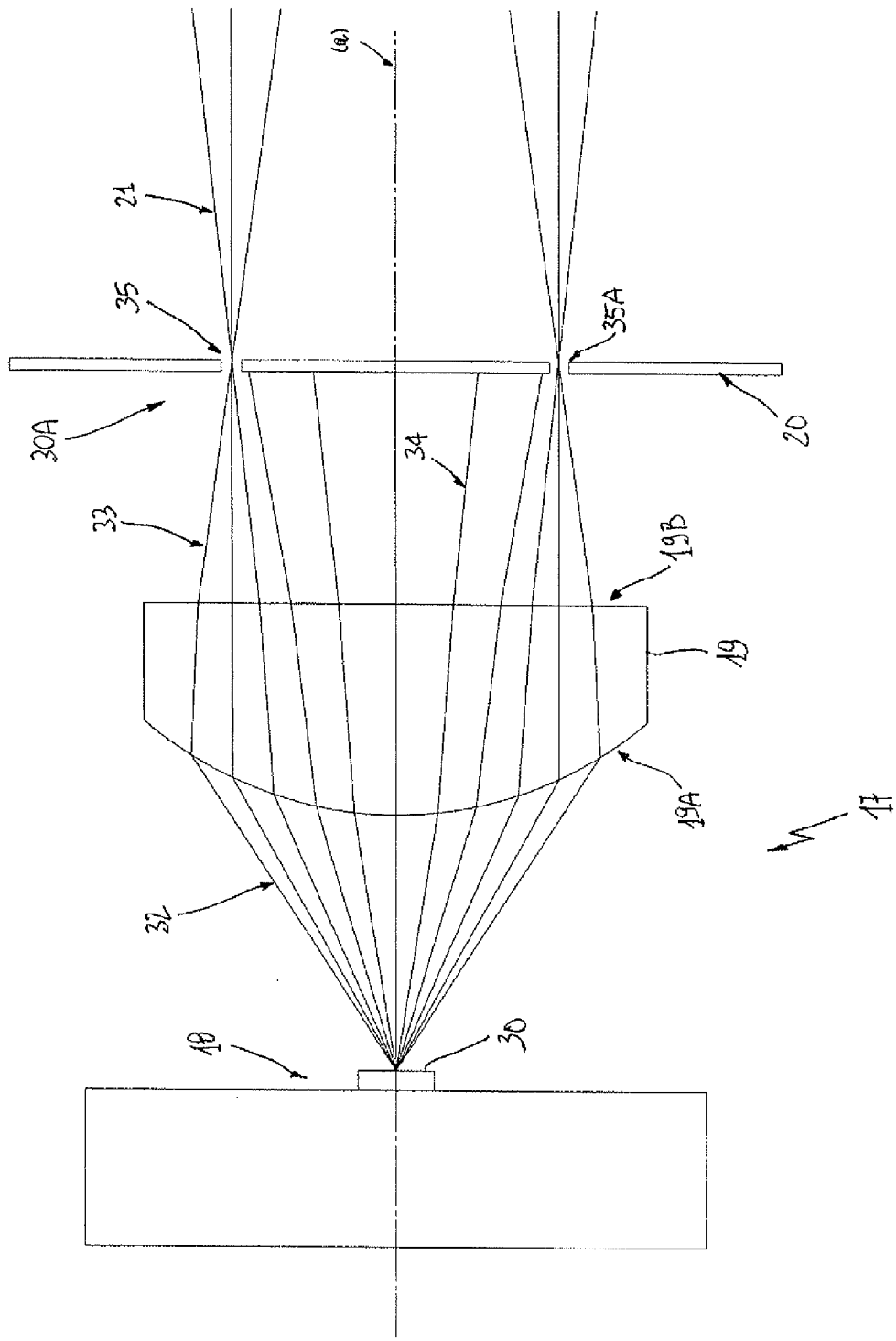
Figure 6:
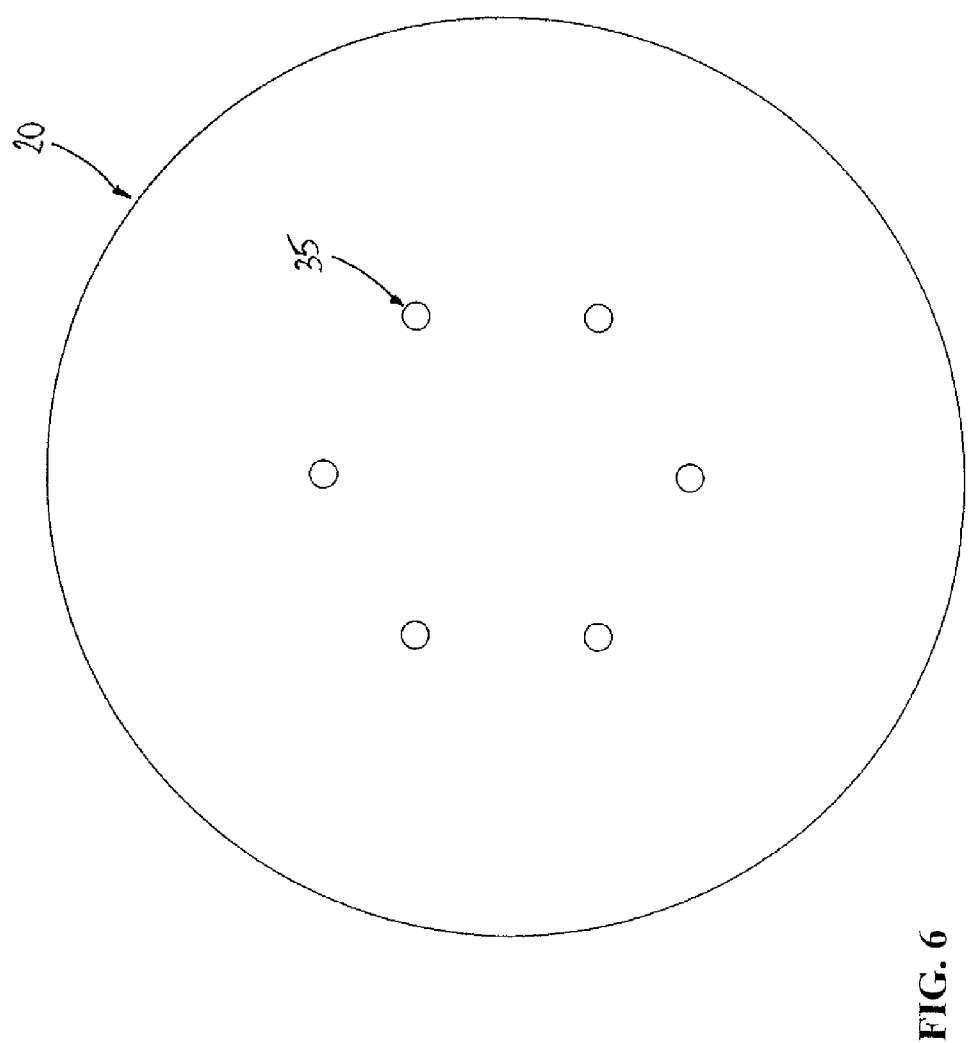
Figure 7:
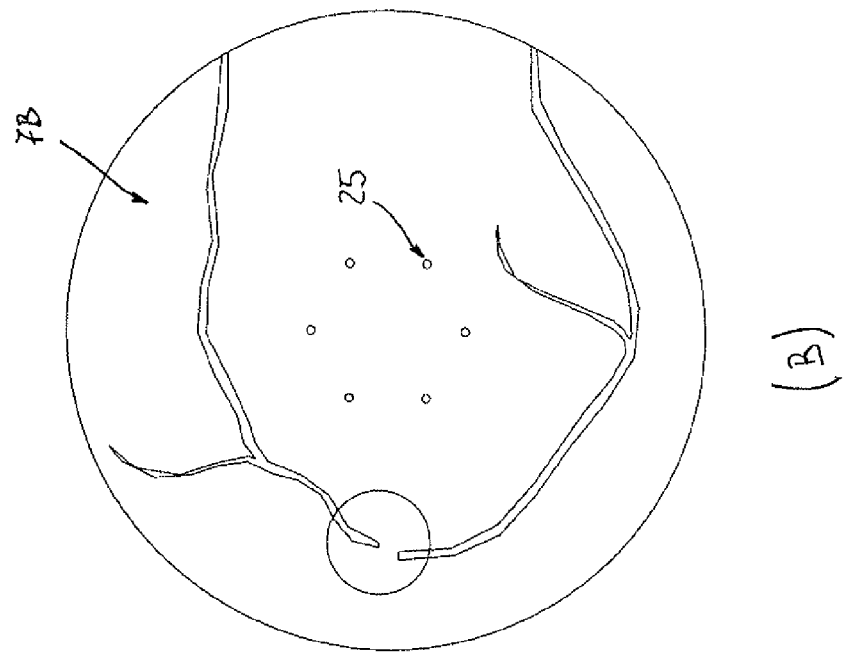
Figure 7:
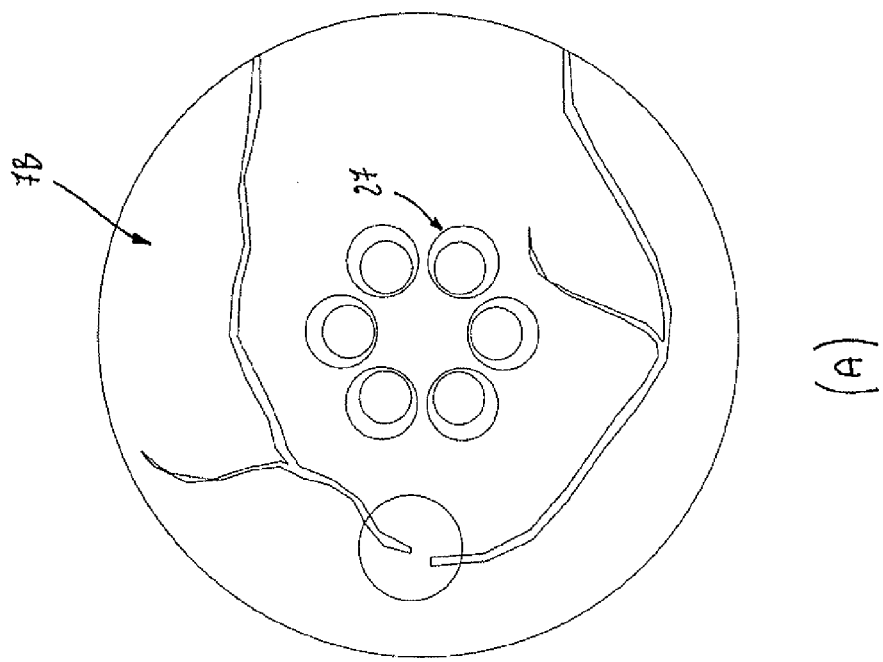
Figure 8:
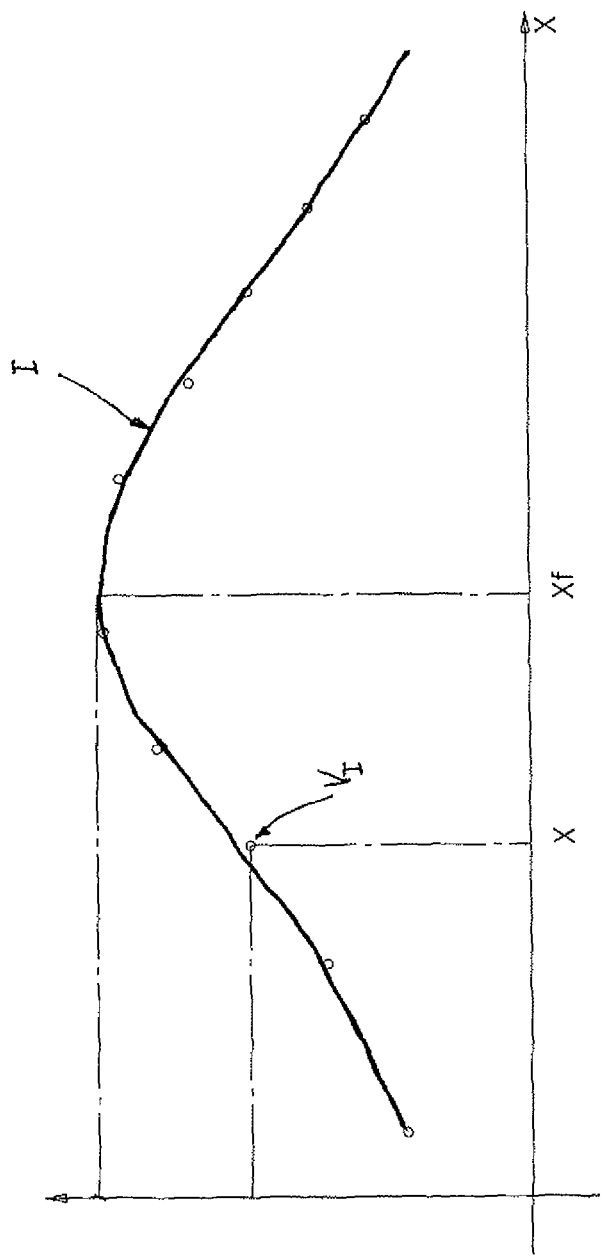
Figure 9:
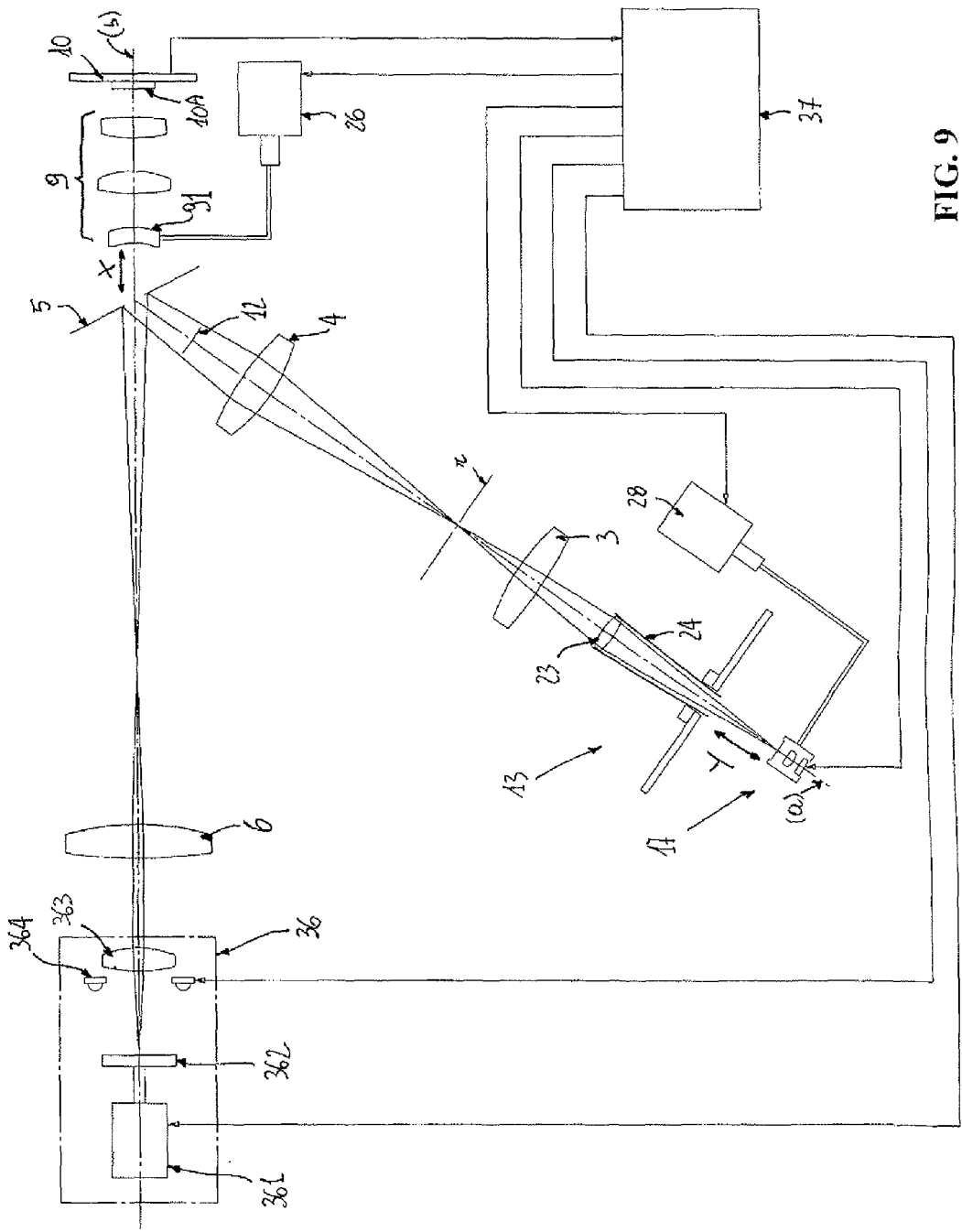
Figure 10:
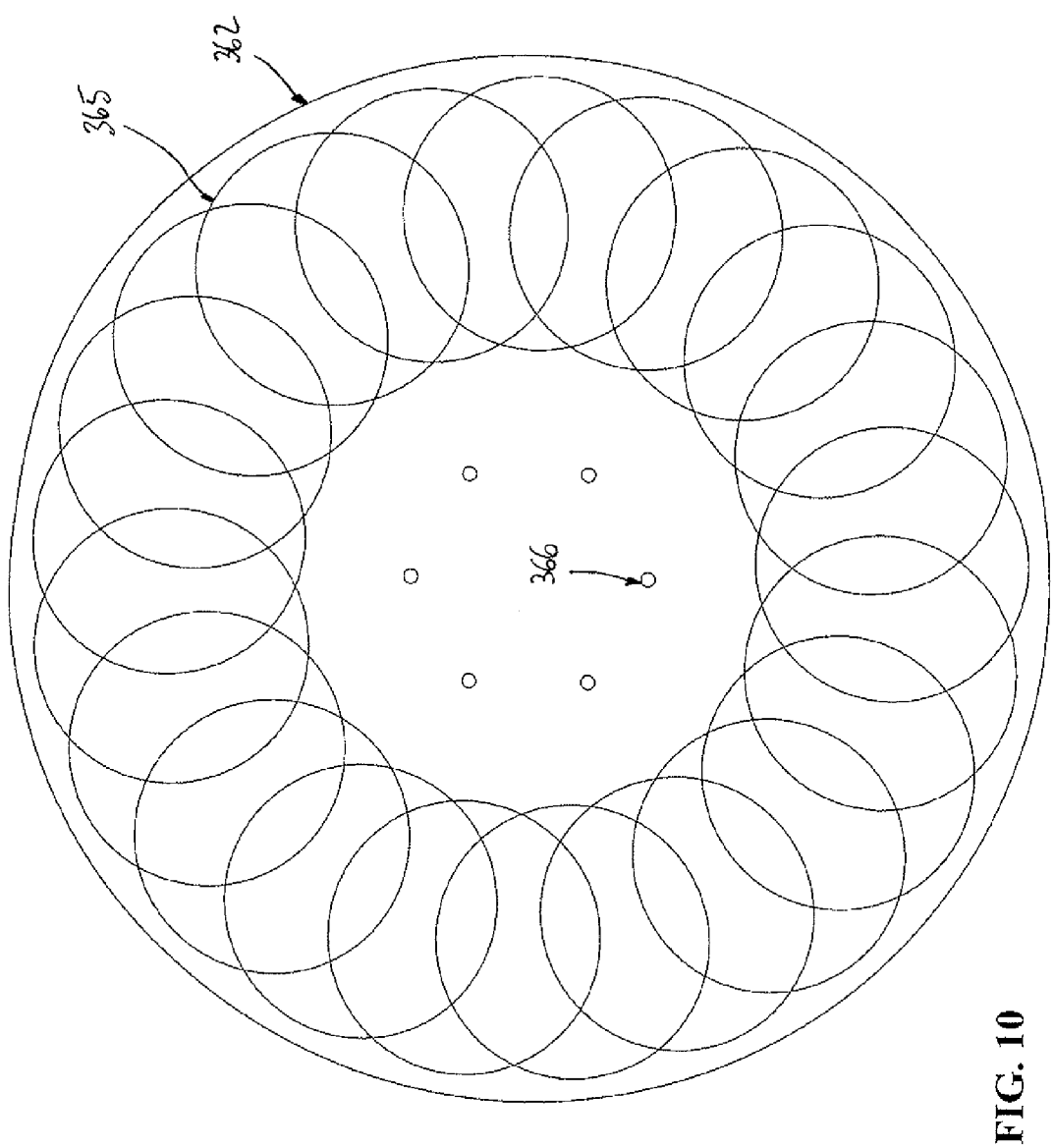
Figure 11:
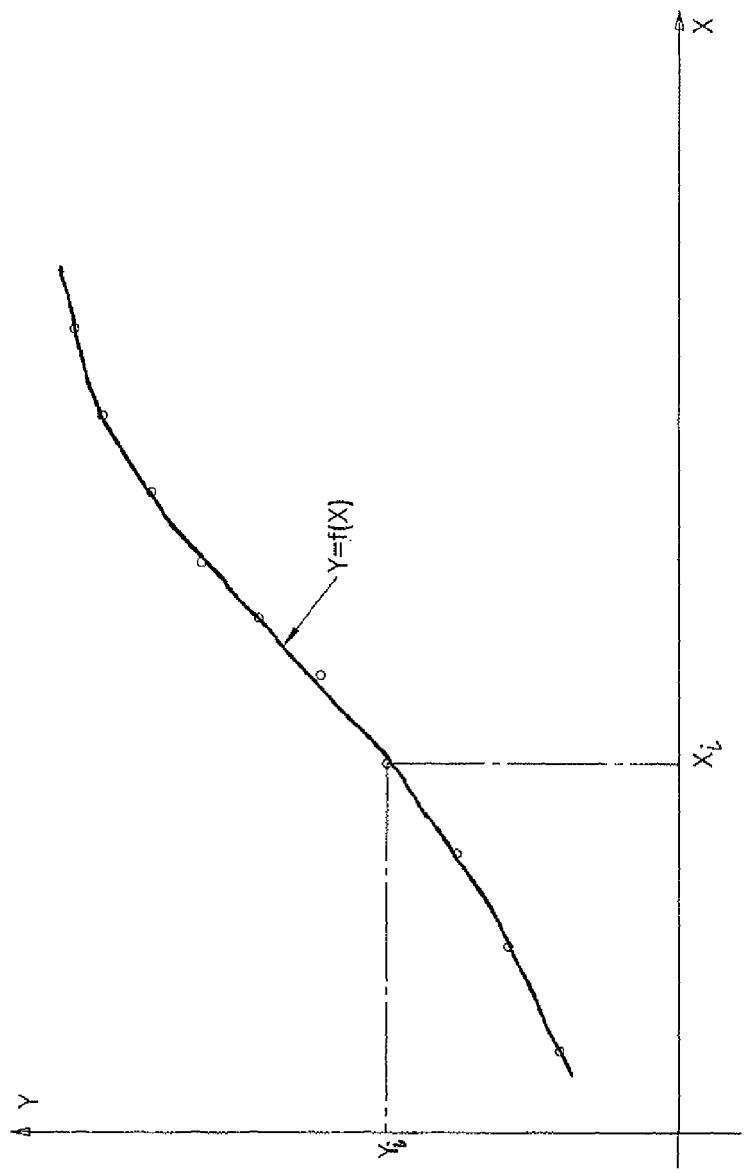

Further characteristics and advantages of the fundus camera according to the invention will become more evident by referring to the description given below and to the figures, attached purely for non-limiting, illustrative purposes, wherein:

FIG. 1 schematically illustrates a fundus camera of known type;

FIG. 2 schematically illustrates the fundus camera according to the present invention, in one of its embodiments;

FIG. 3 schematically illustrates the fundus camera according to the present invention, in another embodiment;

FIG. 4 schematically illustrates the fundus camera according to the present invention, in another embodiment;

FIG. 5 schematically illustrates an embodiment of the projecting means contained in the fundus camera according to the present invention;

FIG. 6 schematically illustrates a detail of the projecting means shown in FIG. 5;

FIG. 7 shows two images of the retina during the focusing procedure for the fundus camera according to the present invention;

FIG. 8 schematically illustrates an example of a variation in the characteristic index calculated in the procedure for focusing the fundus camera according to the present invention;

FIG. 9 schematically illustrates the fundus camera shown in FIG. 3, during the corresponding calibration procedure; and FIG. 10 schematically illustrates a detail of a calibration instrument used during the calibration of the fundus camera shown in FIG. 3;

FIG. 11 schematically illustrates an example of a function calculated in the calibration procedure used for the fundus camera shown in FIG. 3.

With reference to the above-mentioned figures, the present invention refers to a fundus camera 1.

According to the invention, the camera 1 comprises: illuminating means 13, for projecting a first light beam (not shown) to illuminate the retina 7B of a patient's eye 7; projecting means 17, for projecting one or more second light beams 21 onto the retina; sensor means 10, for receiving the light reflected from the retina onto a receiving surface 10A, to acquire one or more images of the retina; and regulating means for adjusting the focus of the images of the retina in line with the receiving surface 10A of the sensor means 10.

The regulating means may, for instance, comprise a movable set of lenses 9 or, preferably, as shown in FIGS. 2-4, a single movable lens 91 in a group of lenses 9.

The camera 1 also comprises actuating means designed to move the regulating means 91 and the projecting means 17.

The actuating means in the camera 1 may comprise a first actuating device 260, preferably consisting of a linear actuator with a stepping motor (FIG. 2).

Alternatively (FIGS. 3-4), the actuating means in the camera 1 may comprise a second actuating device 26, for moving only the regulating means 91, and a third actuating device 28, for moving only the projecting means 17.

The actuating devices 26 and 28 also preferably consist of linear actuators with stepping motors.

In the camera 1, there are also processing means 37 (shown in FIGS. 2-3 only) for analysing the images of the retina acquired by the sensor means 10, and for generating control signals for the above-mentioned actuating means 260, 26, 28.

The illuminating means 13 comprise a one or more first light sources (preferably a plurality of LED devices), which are arranged so that the first light beam emitted by the illuminating means is substantially ring-shaped.

The illuminating means comprise a shaped structure 16A for supporting the first light sources, which comprises a through hole 16, around which the first light sources are preferably arranged.

The shaped structure 16A preferably comprises an electronic card operatively associated with a light concentrating device with a ring-shaped outlet of the type described in the Italian patent application No. TV2009A000201.

Providing it has a through hole 16, the shaped structure 16A may be shaped differently from the one described above.

The first light beam emitted by the illuminating means 13 follows an optical path entirely similar to the one described for the camera in FIG. 1.

As it travels along the optical axis (a) of the illuminating means 13, the first light beam is collimated by means of the lenses 3 and 4 in line with an area that roughly coincides with the centre of a perforated mirror 5.

The first light beam is thus reflected by the mirror 5 along the optical axis (b), and subsequently collimated by means of the one or more lenses 6 at a point situated approximately on the plane of the pupil 7A of the eye 7, thus coming to illuminate the retina 7B.

The light reflected by the retina 7B passes through the central area of the pupil 7A, and is oriented by the lens 6 towards the hole, then it is collimated by means of the set of lenses 9 to form an image on a receiving surface 10A of the sensor means 10, consisting of a digital camera, for instance.

Along the optical path of the first light beam emitted by the illuminating means 13, there is also a mask 12 designed to intercept the light that might give rise to reflections on the cornea of the eye 7.

The projecting means 17 project a plurality of second light beams onto the retina.

They comprise one or more second light sources, preferably at least one infrared light source 18 that can advantageously consist of at least one infrared LED device.

The infrared light source 18 is advantageously associated operatively with an opaque mask 20, with one or more holes 35 that are arranged on a circular zone of the mask to enable the passage of the light 32 emitted by the source 18 (FIGS. 5-6).

The projecting means 17 preferably also comprise an intermediate lens 19 positioned between the infrared light source 18 and the opaque mask 20.

The light 32, emitted from the emission surface 30 of the source 18, is advantageously collimated by means of the lens 19 onto the mask 20.

The lens 19 is mounted so that it has a first surface 19A with a lesser radius facing towards the light source 18, and a second surface 19B with a greater radius facing towards the mask 20.

This particular positioning of the lens 19 considerably increases its spherical aberration.

The diversion of the light rays 33 coming to bear on the peripheral area of the lens 19 is thus greater than the diversion of the light rays 34 coming to bear on areas closer to the centre of the lens 19.

The light rays 32 falling on the lens 19 consequently intersect at an intersection area 30A, in the form of a circular crown, situated a certain distance from the lens 19.

The power density of the light beam 32 emitted by the source 18 reaches its maximum peak in this intersection area 30A.

The mask 20 is advantageously positioned substantially at said intersection area 30A, with the holes 35 arranged in a substantially circular pattern, the diameter of said circle advantageously corresponding to the diameter of the intersection area 30A.

The light rays 32 diverted by the lens 19 advantageously converge before the outer edge 35A of the holes 35 in the mask 20.

The light beams 21 emerging from the holes 35 consequently diverge as if they were generated by independent light sources located in line with the holes 35.

Thanks to this arrangement, the light coming from the projecting means 17 is thus entirely similar to the light created by a plurality of independent sources, each designed to emit a light beam 21.

In this case, however, only one light source 18 and only one collimation lens 19 are used, considerably simplifying the structure of the projecting means 17, with a corresponding reduction in the manufacturing costs.

The intermediate lens 19 is preferably a plano-convex lens. This enables a further cost reduction while obtaining good-quality light beams 21 emerging from the holes 35 in the mask 20.

According to the invention, the projecting means 17 are arranged coaxially to the illuminating means 13, along the same optical axis (a) as the latter.

The projecting means 17 are advantageously arranged so that they project the light beams 21 through the hole 16 in the supporting structure 16A for the illuminating means 13.

The projecting means 17 comprise a collimation lens 23 and a hollow body 24.

The light beams 21 pass through the collimation lens 23, which is supported and maintained in a position coaxial to the illuminating means 13 by the hollow body 24, which is operatively associated with the through hole 16 of the shaped structure 16A.

The hollow body 24 is preferably in the shape of a cylindrical or conical tube that is operatively associated with the through hole 16 at an end that is opposite to the one in which the lens 23 is located.

The walls of the hollow body 24 are advantageously capable of intercepting the light generating reflections on the crystalline lens of the eye 7.

This avoids the need to provide a dedicated mask for said purpose along the optical axis (a).

The light beams 21 then pass through the further collimation lens 3 and is collimated on a plane (r) optically conjugated with the retina 7B.

In the embodiment illustrated in FIGS. 2-4, the light 21 advantageously enters the optical path of the camera 1, coaxially to the through hole 16, without any need to use movable mirrors or beam splitting devices.

According to an alternative embodiment (not shown), the projecting means 17 could be mounted inside the hollow body 24.

In this case, the position of the projecting means 17 along the optical axis (a) might possibly be adjusted by means of a rod passing through the hole 16.

The light beams 21 following the optical path of the camera 1, along the optical axes (a) and (b), and reach the retina 7B, in line with which they form a matrix of luminous points 25 (FIG. 7, image (B)).

The image of the retina with the above-mentioned matrix of luminous points 25 can be viewed and acquired by the sensor means 10.

FIG. 4 shows a possible variant of the present invention, in which a mirror 29 is inserted along the optical path, between the illuminating means 13 and the perforated mirror 5.

This mirror 29 is advantageously designed to reflect the first light beam emitted by the illuminating means 13, and/or the second light beams 21 emitted by the projecting means 17.

The introduction of the mirror 29 enables the optical path between the illuminating means 13 and the perforated mirror 5 to be bent along the optical axis (a).

This enables the structure of the camera 1 to be kept more compact with a significant reduction in its overall dimensions.

Preferably, the processing means 37, consisting of a computer executing one or more computer programs, for instance, are designed to calculate indicative data of the maximum light intensity values in one or more images of the retina acquired by the sensor means 10.

On the base of the data thus calculated, the processing means 37 generate control signals for the actuating means 260, 26 and 38 in order to move the regulating means 91 into a focusing position $X_F$, coinciding with which the retina is optically conjugated with the receiving surface 10A of the sensor means 10.

The data indicating the distribution of the light intensity preferably comprise the same number of maximum light intensity values in the images of the retina as the number of the second beams 21 projected onto the retina.

Theses data indicating the distribution of the points of maximum light intensity can advantageously be characterised by a characteristic index I of the points of maximum light intensity for the images obtained, such as the arithmetic mean of the maximum light intensity values.

An example of a variation in the characteristic index I as a function of the position X of the regulating means 91 is shown in FIG. 8.

The processing means 37 preferably execute a procedure that involves measuring the focusing of the camera 1, analysing a series of images of the retina showing the matrix of luminous points generated by the light beams 21 emitted by the projecting means 17, each of said images corresponding to a certain position X of the regulating means 91, along the axis (b).

The procedure executed by the processing means 37 comprises a step (i), in which the processing means analyse an image of the retina acquired by the sensor means 10, and a step (ii), in which the processing means determine a number points of maximum light intensity in said image of the retina, which is equal to the number of second light beams projected by the projecting means 17.

After establishing the points of maximum light intensity in the image acquired, there is a step (iii) in which a value $V_I$ of a characteristic index I of the points of maximum light intensity is calculated, e.g. the arithmetic mean of the values of maximum light intensity corresponding to the points of maximum light intensity found in the previous step (ii).

Then there is a step (iv) for storing the value $V_I$ of the characteristic index I calculated in step (iii), and the corresponding position X of the regulating means 91, along the optical axis (b). The procedure then involves a step (v), in which the processing means generate control signals for the actuating means 260, 26, 28, in order to move the regulating means 91 and the projecting means 17 in a synchronised manner and with a predefined step.

In the next step (vi), the previous steps from (i) to (v) are repeated at least once.

Thus, as shown in FIG. 8, the trend of the characteristic index I can be reconstructed by identifying a suitable curve that interpolates the set of values $V_I$ calculated for each repetition of the cycle consisting of the previous steps (i) to (v), and for each image acquired.

At a step (vii) the processing means calculate the maximum value $I_{MAX}$ of the characteristic index I, and a step (viii) generate control signals for the actuating means 260, 26, 28, in order to move the regulating means 91 into the position $X_F$, coinciding with which said characteristic index I acquires the maximum value $I_{MAX}$.

The procedure executed by the processing means 37 to focus the camera 1 exploits the fact that the luminous intensity of the points 25 projected onto the retina correlates with the state of collimation of the light beams 21.

In particular, the luminous intensity of the points 25 projected onto the retina increases as a function of the degree of collimation of the light beams 21, reaching the maximum values when the light beams 21 are focused on the retina.

To identify the degree of collimation of the light beams 21 in the image provided by the sensor means 10, the procedure completed by the processing means 37 involves calculating a characteristic index I indicative of the points of maximum light intensity on the pixels of the acquired image (FIG. 8).

This characteristic index I reaches its maximum value $I_{MAX}$ for a position $X_F$ of the regulating means 91, coinciding with which the power of the light beams 21 is distributed over a minimum area, i.e. when the light beams 21 are collimated on the retina.

In this situation, since the regulating means 91 move in a synchronised manner with the emitter 17, the retina is also optically conjugated with the receiving surface 10A of the sensor means 10.

The camera 1 is focused when the regulating means 91 are in the position $X_F$.

The projection of a matrix of luminous points 25 (FIG. 7) inside the eye, rather than a single point, makes the procedure for analysing the acquired images particularly reliable.

In fact, this means that the analysis of the images acquired by the sensor means 10 is substantially unaffected by any presence of local shadows caused, for example, by the presence of blood vessels or defects of the retina.

If only a single point were to be projected, and this point were to be collimated on a blood vessel, for instance, the power density could drop when the luminous point is collimated on an area of narrower diameter than that of the blood vessel.

This could make it difficult to identify the peak collimation of the point.

Projecting a matrix of luminous points reduces the probability of all of the points collimated coinciding with blood vessels or defects of the retina, and the procedure for analysing the images of the retina consequently becomes more reliable.

Initially, the luminous points 25 generally appear as blurred ring-shaped patches of light 27, with a central area that is not illuminated (FIG. 7-*image* (A)).

For an eye with refractory defects (myopia or hypermetropia), the plane conjugated with the sensor means 10, where the light beams 21 are collimated, does not coincide with the surface of the retina.

The ring shape of the patches of light 27 is substantially due to the presence of the mask 12 along the optical path that not only intercepts the light that would be reflected on the cornea and from there onto the sensor means 10, it also intercepts the central portion of the light beams 21 that generate the luminous points 25.

Moving the regulating means 91 and the projecting means 17 in a synchronised manner makes the blurred patches of light 27 become collimated into the luminous points 25.

Continuing to move the regulating means 91 and the projecting means 17 makes the luminous points become blurred ring-shaped patches again.

The ring-shaped cross-section of the light beams 21 facilitates an increase in the variation of the light intensity on the pixels of the receiving surface 10A of the sensor means 10 during the search for the position of maximal collimation, thus making the focusing procedure more precise.

This derives from the fact that the ring-shaped light beams 21 have no central light rays, which would become less blurred than the peripheral rays during any displacement of the projecting means 17.

To make the above-described procedure less time consuming, the processing means 37 could advantageously measure the power density of the pixels on the receiving surface 10A in line with a certain number of software windows centred with the nominal position of the luminous points 25, thus avoiding the need to analyse the whole image acquired by the sensor means 10.

The above procedure is easy to implement automatically by means of software program resident in the memory of the processing means 37.

In the light of the above, a further aspect of the invention clearly concerns a method for focusing the fundus camera 1.

The above focusing method involves at least the following steps:

I) projecting the second light beams 21 onto the retina by means of the projecting means 17;
II) acquiring an image of the retina with the sensor means 10;
III) determining a number points of maximum light intensity in the image of the retina acquired in step (II), which is equal to the number of said light beams that are projected by the projecting means 17;
IV) calculating a value $V_I$ of a characteristic index I of the points of maximum light intensity;
V) moving the regulating means 91 and the projecting means 17 in a synchronised manner and with a predefined step;
VI) repeating the previous steps from (I) to (V) at least once;
VII) calculating the maximum value $I_{MAX}$ of the characteristic index I;
VIII) moving the regulating means 91 into the position $X_F$ coinciding with which the characteristic index I acquires the maximum value $I_{MAX}$.

The actuating means 260, 26, 28 of the camera 1 preferably move the regulating means 91 and the projecting means 17 so that the displacement of the regulating means 91 is mechanically synchronised with the displacement of the projecting means according to a function $Y=f(X)$, where X is the position of the regulating means 91 along the axis (b), and Y is the position of the projecting means 17 along the axis (a).

This ensures that the area of maximum collimation of the luminous points 25 projected inside the eye 7 by the projecting means 17 is always on a plane situated in the vicinity of the retina 7B, conjugated with the receiving surface 10A of the sensor means 10.

According to one embodiment of the present invention (FIG. 2), the regulating means 91 and the projecting means 17 are operatively connected together by a kinematic chain 38, which may consist, for instance, of a system of levers or a cam mechanism.

The kinematic chain 38 is operatively connected to the one actuating device 260, which can thus adjust the position X of the regulating means 91 along the axis (b) in a manner synchronised with the position Y of the projecting means 17 along the axis (a).

Alternatively (FIGS. 3-4), the camera 1 can comprise the independent actuating devices 26 and 28, and controlled by the processing means 17 in order to move the regulating means 91 and projecting means 17 in a synchronised manner.

According to said variant, the synchronised displacement of the regulating means 91 and of the projecting means 17 is clearly obtained not mechanically, by means of a kinematic chain connecting the parts in motion to one another, but by a software program executed by the processing means 37.

In this case, the previously-mentioned function $Y=f(X)$ can advantageously be established by means of suitable calibration procedure on the camera 1.

This has several advantages.

For instance, the optics for the camera 1 can be designed virtually independently from the design of the mechanical parts, enabling a reduction in the time and cost of designing or modifying the camera 1.

It is also possible to establish the function $Y=f(X)$, adjusting for the tolerances of the mechanical and optical parts, unlike the case of the other embodiments of the present invention involving the use of a kinematic chain 38.

In the latter cases, in fact, the function Y=f(X) is calculated starting from the nominal dimensions of the optical and mechanical parts, and this could lead to synchronisation errors between the positions X and Y due to the tolerances involved.

In the embodiment of the present invention shown in FIGS. 3-4, the tolerances of the mechanical and optical parts can consequently be increased without affecting the operation of the camera 1, thus enabling a reduction in its overall costs.

The above-described calibration procedure involves a first step (a) of providing a calibration instrument comprising a lens 363 and a moving target 362, coaxial to the lens 363.

The axial position of the target 362 in relation to the lens 363 can be adjusted by means of a fourth actuating device 361, consisting of a linear actuator with a stepping motor, for instance, advantageously controlled by the processing means 37.

The surface of the target 362 has a high-contrast pattern 365, such as a number of repeated geometrical figures consisting of black lines on a white background (FIG. 10).

The pattern 365 is advantageous for focusing the sensor means 10 during the calibration process, using algorithms of known type that identify the clearest image from among a series of images obtained.

The light beams 21, emitted by the projecting means 17, are advantageously projected onto the central part of the target 362, generating the luminous points 366.

The central part of the target 362 is advantageously of only one colour (e.g. white) to facilitate the identification of the local peak intensities of the luminous points projected during the calibration procedure.

The target 362 can be illuminated with the illuminating means 13 or by means of any other illuminator device 364, incorporated in the calibration instrument 36.

The calibration procedure then involves a step (b) for fitting the calibration instrument 36 in a predefined position in relation to the lens 6, i.e. in front of the latter.

Then there is a step (c) for preparing the actuating means 26 and 28, and the actuating device 361 in a zero starting position, followed by a step (d) for illuminating the target 362 and deactivating the projecting means 17.

The target 362 can be illuminated with the light beam normally used by the illuminating means 13 to illuminate the retina or, preferably, with a light beam generated by means of the illuminator device 364.

Adopting the illuminator device 364 avoids the need to make the light pass through the lenses in the objective lens 363. This eliminates any risk of reflections of this light being generated on the lenses of the objective 363.

The calibration procedure also involves a step (e) for acquiring first images of the target 362 for different positions X of the regulating means 91 along the axis (b), with the aid of the sensor means 10.

Then there is a step (f) for analysing said first images, identifying and storing the position Xi of the regulating means 91 corresponding to the clearest image among those examined.

In step (g) of the calibration procedure, the illuminating means 13 or illuminator device 364 are deactivated and the projecting means 17 are activated.

Then, in step (h), the sensor means 10 acquire second images of the target 362 for different positions Y of the projecting means 17 along the axis (a), while maintaining the regulating means 91 in the position Xi.

Afterwards, in step (i), the calibration procedure involves identifying the points of maximum light intensity for each of the second images acquired and calculating a characteristic index I of said points of maximum light intensity.

This is followed by a step (j) for calculating the maximum value $I_{MAX}$ of said characteristic index, step (k) for identifying and storing the position (Yi) of the projecting means 17 coinciding with which the characteristic index acquires said maximum value, and step (l) for storing the pair of positions (Xi, Yi).

In step (m), the procedure involves moving the target 362 with a predefined step by means of the fourth actuating device 361.

Then, in step (n), all the previous steps from (d) to (m) are repeated at least once.

We thus obtain a set of pairs (Xi, Yi) relating to a plurality of possible synchronised positions for the regulating means 91 and projecting means 17.

Finally, the calibration procedure includes a step (o) for calculating the function Y=f(X) governing the synchronized positioning of the regulating means 91 and projecting means 17, on the strength of the data saved at the previous steps, i.e. the set of pairs (Xi, Yi) identified in the calibration procedure.

The camera 1 according to the invention has considerable advantages over the known art.

The procedure for focusing the camera 1 is very straightforward and reliable. The projection of a plurality of luminous points onto the retina ensures that the results are virtually unaffected by any local defects of the retina or any presence of blood vessels.

The focusing procedure is consequently easy to complete automatically with the aid of suitable software, which can be run by the processing means 37.

The camera 1 is characterised by a marked structural simplicity.

The projecting means 17 have a relatively straightforward structure and do not comprise any complex systems of microprisms and lenses for generating the light beams 21.

Inside the camera 1, the light beams 21 emitted by the projecting means 17 are inserted in the optical path without using movable mirrors or beam splitting devices.

In one embodiment, the camera 1 can easily be adjusted by means of a preset calibration procedure that enables the risk of human error to be reduced and also contains the time and cost of the camera's manufacture.

The camera 1 is very compact and is of relatively limited weight and overall dimensions.

It is clear from the above description that the camera 1 is globally of relatively straightforward structural design, easy to manufacture on an industrial scale, and offers considerable advantages in terms of contain production costs.

The invention claimed is:

1. A fundus camera comprising:
    illuminating means that project a first light beam to illuminate the retina of a patient's eye, said illuminating means comprising one or more first light sources operatively associated with a ring-shaped structure provided with a through hole;
    projecting means that project one or more second light beams on the patient's retina, said projecting means comprising one or more second light sources;
    sensor means that receive the light reflected by the patient's retina at a receiving surface, so as to acquire one or more images of the patient's retina;
    regulating means that regulate the focusing of the images of the patient's retina, at the receiving surface of said sensor means;
    actuating means that move said regulating means and said projecting means;

processing means that analyze the images of the patient's retina, acquired by said sensor means, and generate control signals for said actuating means;

a lens mounted in a hollow body connected to and coaxially aligned with the through hole;

said projecting means is coaxial with said illuminating means, along a same axis (a), and project light beams from at least one of the second light sources through hole and then the lens.

2. Fundus camera, according claim 1, wherein said hollow body is shaped as a cylindrical or conical tube.

3. Fundus camera, according to claim 2, wherein said processing means calculate data related to the values of maximum light intensity in one or more images of the patient's retina, said processing means generating, on the base of said data indicative of the values of maximum light intensity, control signals for said actuating means, so as to move said regulating means in a focusing position ($X_F$), at which the patient's retina is optically conjugated with the receiving surface of said sensor means.

4. Fundus camera, according to claim 2, wherein said actuating means comprise a first actuating device operatively connected to a kinematic chain aimed at operatively connecting said regulating means and said projecting means, so as to move said regulating means and said projecting means in a synchronised manner, according to a function $Y=f(X)$, where X is the position of said regulating means and Y is the position of said projecting means.

5. Fundus camera, according to claim 2, wherein said actuating means comprise a second actuating device to move said regulating means and a third actuating device to move said projecting means, said processing means generating control signals for said second and third actuating devices, so as to move said regulating means and said projecting means in a synchronised manner, according to a function $Y=f(X)$, where X is the position of said regulating means and Y is the position of said projecting means.

6. Fundus camera, according to claim 1, wherein said processing means calculate data related to the values of maximum light intensity in one or more images of the patient's retina, said processing means generating, on the base of said data indicative of the values of maximum light intensity, control signals for said actuating means, so as to move said regulating means in a focusing position ($X_F$), at which the patient's retina is optically conjugated with the receiving surface of said sensor means.

7. Fundus camera, according to claim 6, wherein said processing means:

i) analyze an image of the patient's retina acquired by said sensor means;

ii) determine a number of points of maximum light intensity in said image of the patient's retina, which is equal to the number of the second light beams projected by said projecting means;

iii) calculate a value ($V_I$) of a characteristic index of said the points of maximum light intensity;

iv) store the value of said characteristic index, calculated at said step iii), and the related position of said regulating means;

v) generate control signals for said actuating means so as to move in a synchronized manner and with a predefined step said regulating means and said projecting means;

vi) repeat at least once the previous steps i)-v);

vii) calculate the maximum value ($I_{MAX}$) of said characteristic index;

viii) generate control signals for said actuating means so as to move said regulating means in a position ($X_F$), at which said characteristic index has said maximum value.

8. Fundus camera, according to claim 7, wherein said actuating means comprise a first actuating device operatively connected to a kinematic chain aimed at operatively connecting said regulating means and said projecting means, so as to move said regulating means and said projecting means in a synchronised manner, according to a function $Y=f(X)$, where X is the position of said regulating means and Y is the position of said projecting means.

9. Fundus camera, according to claim 7, wherein said actuating means comprise a second actuating device to move said regulating means and a third actuating device to move said projecting means, said processing means generating control signals for said second and third actuating devices, so as to move said regulating means and said projecting means in a synchronised manner, according to a function $Y=f(X)$, where X is the position of said regulating means and Y is the position of said projecting means.

10. Fundus camera, according to claim 6, wherein said actuating means comprise a first actuating device operatively connected to a kinematic chain aimed at operatively connecting said regulating means and said projecting means, so as to move said regulating means and said projecting means in a synchronised manner, according to a function $Y=f(X)$, where X is the position of said regulating means and Y is the position of said projecting means.

11. Fundus camera, according to claim 6, wherein said actuating means comprise a second actuating device to move said regulating means and a third actuating device to move said projecting means, said processing means generating control signals for said second and third actuating devices, so as to move said regulating means and said projecting means in a synchronised manner, according to a function $Y=f(X)$, where X is the position of said regulating means and Y is the position of said projecting means.

12. Fundus camera, according to claim 1, wherein said actuating means comprise a first actuating device operatively connected to a kinematic chain aimed at operatively connecting said regulating means and said projecting means, so as to move said regulating means and said projecting means in a synchronised manner, according to a function $Y=f(X)$, where X is the position of said regulating means and Y is the position of said projecting means.

13. A method for focusing a fundus camera, according to claim 1, on the retina of the patient's eye, wherein it comprises the following steps:

I) projecting second light beams on the patient's retina by means of said projecting means;

II) acquiring an image of the patient's retina;

III) determining a number of points of maximum light intensity in said image of the patient's retina, which is equal to the number of the second light beams projected by said projecting means;

IV) calculating a value ($V_I$) of a characteristic index (I) of said points of maximum light intensity;

V) moving said regulating means and said projecting means in a synchronised manner and with a predefined step;

VI) repeating at least once the previous steps I)-V);

VII) calculating the maximum value ($I_{MAX}$) of said characteristic index;

VIII) moving said regulating means in a position ($X_F$), at which said characteristic index has said maximum value.

14. The fundus camera of claim 1, wherein the hollow body shields the lens from light from the one or more first light sources.

15. A fundus camera, comprising:
   illuminating means that project a first light beam to illuminate the retina of a patient's eye, said illuminating means comprising one or more first light sources operatively associated with a shaped structure provided with a through hole;
   projecting means that project one or more second light beams on the patient's retina, said projecting means comprising one or more second light sources;
   sensor means that receive the light reflected by the patient's retina at a receiving surface, so as to acquire one or more images of the patient's retina;
   regulating means that regulate the focusing of the images of the patient's retina, at the receiving surface of said sensor means;
   actuating means that move said regulating means and said projecting means;
   processing means that analyze the images of the patient's retina, acquired by said sensor means, and generate control signals for said actuating means;
characterized in that said projecting means are arranged coaxially with said illuminating means, along a same axis (a), and project said second light beams through at least a lens that is kept in position by a hollow body, which is operatively associated ti said through hole;
wherein said projecting means comprise at least a second infrared light source, an opaque mask provided with one or more holes, which are arranged on a substantially circular zone of said mask to allow the passage of the light emitted by said infrared light source, and a lens, which is positioned between said infrared light source and said opaque mask, said lens being arranged so as to have a first surface, with a minor radius, facing towards said infrared light source, and a second surface, with a major radius, facing towards said opaque mask.

16. Fundus camera, according claim 15, wherein said hollow body is shaped as a cylindrical or conical tube.

17. Fundus camera, according to claim 15, wherein said processing means calculate data related to the values of maximum light intensity in one or more images of the patient's retina, said processing means generating, on the base of said data indicative of the values of maximum light intensity, control signals for said actuating means, so as to move said regulating means in a focusing position ($X_F$), at which the patient's retina, is optically conjugated with the receiving surface of said sensor means.

18. Fundus camera, according to claim 15, wherein said actuating means comprise a first actuating device operatively connected to a kinematic chain aimed at operatively connecting said regulating means and said projecting means, so as to move said regulating means and said projecting means in a synchronised manner, according to a function $Y=f(X)$, where X is the position of said regulating means and Y is the position of said projecting means.

19. Fundus camera, according to claim 15, wherein said actuating means comprise a second actuating device to move said regulating means and a third actuating device to move said projecting means, said processing means generating control signals fir said second and third actuating devices, so as to move said regulating means and said projecting means in a synchronised manner, according to a function $Y=f(X)$, where X is the position of said regulating means and Y is the position of said projecting means.

20. A fundus camera, comprising:
   illuminating means that projects a first light beam to illuminate the retina of a patient's eye, said illuminating means comprising one or more first light sources operatively associated with a shaped structure provided with a through hole;
   projecting means that project one or more second light beams on the patient's retina, said projecting means comprising one or more second light sources;
   sensor means that receive the light reflected by the patient's retina at a receiving surface, so as to acquire one or more images of the patient's retina;
   regulating means that regulate the focusing of the images of the patient's retina, at the receiving surface of said sensor means;
   actuating means that move said regulating means and said projecting means;
   processing means that analyze the images of the patient's retina, acquired by said sensor means, and generate control signals for said actuating means;
wherein said actuating means comprise a second actuating device to move said regulating means and a third actuating device to move said projecting means, said processing means generating control signals for said second and third actuating devices, so as to move said regulating means and said projecting means in a synchronised manner, according to a function $Y=f(X)$, where X is the position of said regulating means and Y is the position of said projecting means.

21. Fundus camera, according claim 20, wherein said function $Y=f(X)$ is calculated by:
   a) providing a calibration instrument comprising a lens, a moving target, coaxial with said lens, the axial position of said target, with respect to said lens, being able to be regulated by means a fourth actuating device;
   b) mounting said calibration instrument in predefined position with respect to a lens of said fundus camera;
   c) arranging said actuating means and said fourth actuating device in a zero starting position;
   d) illuminating said target, by means of said illuminating means or an illuminating device, and deactivating said projecting means;
   e) acquiring by means of said sensor means first images of said target for different positions (X) of said regulating means;
   f) analyzing said first images, identifying and storing the position (Xi) of said regulating means, corresponding to the image having maximum brightness among said first images;
   g) deactivating said illuminating mean or said illuminating device and activating said projecting means;
   h) acquiring by means of said sensor means second images of said target for different positions (Y) of said projecting means, while maintaining said regulation means in said position (Xi);
   i) identifying for each of said second images the points of maximum light intensity and calculating a characteristic index (I) of the points of maximum light intensity;
   j) calculating the maximum value ($I_{MAX}$) for said characteristic index;
   k) identifying and storing a position (Yi) of said projecting means, at which said in characteristic index has said maximum value;
   l) storing the position couple (Xi, Yi);
   m) moving said target by means of said fourth actuating device;
   n) repeating at least once the previous steps d)-m);
   o) calculating, on the base of the data stored at the previous steps, the function $Y=f(X)$, which regulates the synchronised positioning of said regulating means and said projecting means, where X is the position of said regulating means and Y is the position of said projecting means.

22. A fundus camera comprising:
illuminating means that projects a first light beam to illuminate the retina of a patient's eye, said illuminating means comprising one or more first light sources operatively associated with a shaped structure provided with a through hole;
projecting means that project one or more second light beams on the patient's retina, said projecting means comprising one or more second light sources;
sensor means that receive the light reflected by the patient's retina at a receiving surface, so as to acquire one or more images of the patient's retina;
regulating means that regulate the focusing of the images of the patient's retina, at the receiving surface of said sensor means;
actuating means that move said regulating means and said projecting means;
processing means that analyze the images of the patient's retina, acquired by said sensor means, and generate control signals for said actuating means;
wherein said projecting means are arranged coaxially with said illuminating means, along a same axis, and project said second light beams through at least a lens that is kept in position by a hollow body, which is operatively associated to said through hole;
wherein said processing means calculate data related to the values of maximum light intensity in one or more images of the patient's retina, said processing means generating, on the base of said data indicative of the values of maximum light intensity, control signals for said actuating means, so as to move said regulating means in a focusing position, at which the patient's retina is optically conjugated with the receiving surface of said sensor means.

23. A fundus camera comprising:
illuminating means that project a first light beam to illuminate the retina of a patient's eye, said illuminating means comprising one or more first light sources;
projecting means that project one or more second light beams on the patient's retina, said projecting means comprising one or more second light sources;
sensor means that receive the light reflected by the patient's retina at a receiving surface, so as to acquire one or more images of the patient's retina;
regulating means that regulate the focusing of the images of the patient's retina, at the receiving surface of said sensor means;
actuating means that move said regulating means and said projecting means;
processing means that analyze the images of the patient's retina, acquired by said sensor means, and generate control signals for said actuating means;
wherein said processing means calculate data related to the values of maximum light intensity in one or more images of the patient's retina, said processing means generating, on the base of said data indicative of the values of maximum light intensity, control signals for said actuating means, so as to move said regulating means in a focusing position, at which the patient's retina is optically conjugated with the receiving surface of said sensor means.

* * * * *